(12) United States Patent
Bullis et al.

(10) Patent No.: US 9,730,777 B2
(45) Date of Patent: Aug. 15, 2017

(54) SIMPLIFIED PROTOCOL FOR FIXED IMPLANT RESTORATIONS USING INTRA-ORAL SCANNING AND DENTAL CAD/CAM

(71) Applicant: James R. Glidewell Dental Ceramics, Inc., Newport Beach, CA (US)

(72) Inventors: Grant Stewart Bullis, Newport Beach, CA (US); Shawn Andrews Ramirez, Santa Ana, CA (US); Zachary Richard Dalmau, Fountain Valley, CA (US)

(73) Assignee: James R. Glidewell Dental Ceramics, Inc., Newport Beach, CA (US)

(*) Notice: Subject to any disclaimer, the term of this patent is extended or adjusted under 35 U.S.C. 154(b) by 518 days.

(21) Appl. No.: 14/200,689

(22) Filed: Mar. 7, 2014

(65) Prior Publication Data

US 2014/0255873 A1    Sep. 11, 2014

Related U.S. Application Data

(60) Provisional application No. 61/774,826, filed on Mar. 8, 2013.

(51) Int. Cl.
    *G06F 19/00* (2011.01)
    *A61C 13/01* (2006.01)
    (Continued)

(52) U.S. Cl.
    CPC ........... *A61C 13/01* (2013.01); *A61C 8/0048* (2013.01); *A61C 13/0004* (2013.01); *A61C 13/0013* (2013.01)

(58) Field of Classification Search
    CPC ...................................... A61C 13/01
    (Continued)

(56) References Cited

U.S. PATENT DOCUMENTS 5,857,853 A * 1/1999 van Nifterick .... A61C 13/0004
                                                    433/173
6,322,359 B1 * 11/2001 Jordan ................... A61C 11/00
                                                    433/73

(Continued)

FOREIGN PATENT DOCUMENTS

WO    WO2012061652 A2    5/2012
WO    WO2012061655 A2    5/2012
(Continued)

OTHER PUBLICATIONS

Van Noort, Richard. "The future of dental devices is digital." Dental materials 28.1 (2012): pp. 3-12.*

(Continued)

*Primary Examiner* — Satish Rampuria
(74) *Attorney, Agent, or Firm* — Dianne Burkhard

(57) ABSTRACT

A method of creating implant-supported dentures without physical impressions is provided. Digital impressions may be obtained from scanning the oral cavity, its structures, landmarks, and implant positions. These scans together provide a highly accurate, digital model from which a digital patient model may be designed. Digital denture designs may be reproduced as denture shapes by automated manufacturing processes, and an implant-supported denture may be manufactured therefrom. Methods form making a try-in denture and a final implant-supported denture are provided.

22 Claims, 14 Drawing Sheets

(51) Int. Cl.
*A61C 8/00* (2006.01)
*A61C 13/00* (2006.01)

(58) Field of Classification Search
USPC ...... 700/95–102; 433/167–201.1, 199.1, 213
See application file for complete search history.

(56) References Cited

U.S. PATENT DOCUMENTS

| | | | |
|---|---|---|---|
| 6,364,660 B1 * | 4/2002 | Durbin | A61C 9/00 433/213 |
| 6,882,894 B2 * | 4/2005 | Durbin | A61C 13/0004 433/213 |
| 8,352,060 B2 | 1/2013 | Chun et al. | |
| 8,406,909 B2 | 3/2013 | Yau et al. | |
| 2010/0151417 A1 * | 6/2010 | Nilsson | G06F 19/3437 433/167 |
| 2013/0209962 A1 | 8/2013 | Thompson et al. | |

FOREIGN PATENT DOCUMENTS

| | | |
|---|---|---|
| WO | WO2012061659 A2 | 5/2012 |
| WO | WO2012061660 A2 | 5/2012 |

OTHER PUBLICATIONS

Pradies, Guillermo, et al. "Clinical evaluation comparing the fit of all-ceramic crowns obtained from silicone and digital intraoral impressions based on wavefront sampling technology." Journal of dentistry 43.2 (2015): pp. 201-208.*

* cited by examiner

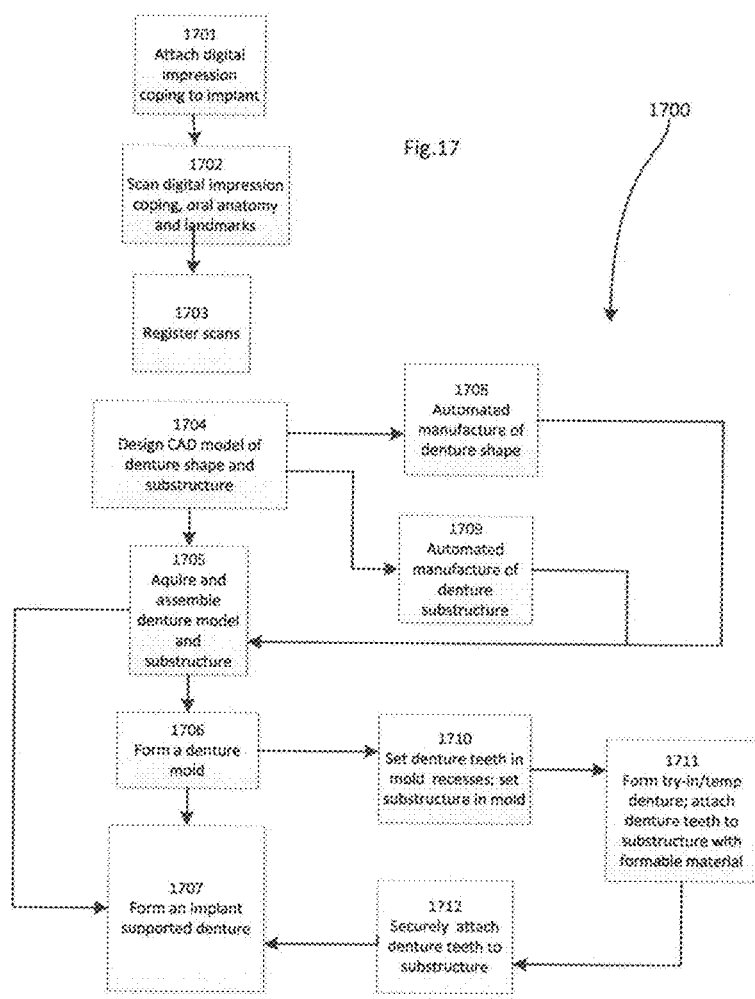

SIMPLIFIED PROTOCOL FOR FIXED IMPLANT RESTORATIONS USING INTRA-ORAL SCANNING AND DENTAL CAD/CAM

CROSS-REFERENCE TO RELATED APPLICATIONS

This application claims the benefit of U.S. Provisional Application No. 61/774,826, filed Mar. 8, 2013, which is incorporated by reference herein in its entirety.

FIELD

This disclosure generally relates to a method of creating implant denture restorations using digitized impressions of the oral cavity rather than from physical laboratory models and impressions.

BACKGROUND

Methods to create implant denture restorations by means of physical impressions and laboratory models are well documented in the dental literature. According to one technique, a series of appointments are conducted at the dental office. An appointment for physical impressions followed by appointments for jaw relation records, denture try-ins, verification jigs, final impressions, denture setup try-ins and the delivery of the final prosthesis are necessary to complete treatment. The large number of appointments required, and the amount of time consumed between appointments by shipping the restorative components between the doctor and the dental laboratory, make the implant denture restorative process expensive and time consuming.

Other problems arise from cumulative error in the impression and subsequent models and restorations derived from the impression. Digital impressions are not subject to degradation of impression accuracy during subsequent steps of the restorative process.

SUMMARY

A method of creating implant-supported dentures without physical impressions is provided. In one embodiment, digital impressions are used in place of physical impressions to form implant-supported denture devices, and a method for obtaining digital impressions is provided. Digital impressions may be obtained by scanning the oral cavity of a patient, including its structures and the positions of implants that have been implanted in a patient's oral anatomy.

In an embodiment, dentition, occlusal records and anatomical features of a patient are scanned. The implant position and axis of the implant are captured digitally by scanning of digital impression copings in the mouth. These scans are registered together to provide a highly accurate, digital model from which a denture can be manufactured.

In one embodiment, a series of scans are taken in the doctor's office, sent to the laboratory, and a denture shape and supporting substructure are designed with a dental CAD (computer-aided design) program. The substructure may be milled, and the denture shape may be made by an additive manufacturing process, such as by printing on a three-dimensional (3D) printer. The substructure and denture shape are combined to form an assembly, and a denture mold is made from the assembly. The printed denture shape is removed from the mold, and denture teeth are put in the corresponding recesses in the mold, and then fixed to the substructure with wax or equivalent fixation material.

A try-in denture created by this process may be sent to the doctor's office to check the fit of the substructure and denture teeth in the patient's mouth. The doctor may make any adjustments necessary and return the try-in denture to the dental laboratory where it is processed into a final denture restoration.

In a further embodiment, as an alternative to additive manufacturing, the denture shape may be milled from a compliant substrate, and the denture shape and the substrate are combined to create the try-in denture. In one embodiment, the implant-supported denture device is a monolithic component, wherein the denture shape is milled from a material that does not require a supporting substructure.

In another embodiment, a dental laboratory may choose to process the denture shape and substructure into the final implant-supported denture restoration without an intermediate try-in denture.

In an embodiment, the final denture gingival material may be milled into shape, and the denture teeth and substructure then combined, or it may be combined with the denture teeth and substructure through conventional laboratory methods.

In an alternate embodiment, the substructure may be manufactured through an additive process such as electron beam melting or selective laser sintering before incorporating into the restoration.

In a further embodiment, an implant-supported denture device may comprise a denture shape comprising a material that does not require a separate supporting substructure. In one embodiment, the implant-supported denture device comprises a self-supporting monolithic denture shape having denture teeth and denture gingiva that has been milled from a ceramic, such as zirconia.

In one embodiment, the implant-supported prosthesis is a fixed-implant denture.

BRIEF DESCRIPTION OF THE DRAWINGS

The aforementioned embodiments, as well as additional embodiments and advantages thereof, will be more fully understood hereinafter as a result of a detailed description of various embodiments when taken in conjunction with the following drawings.

FIG. 17 shows a block diagram of an embodiment described herein.

While the above-identified drawings set forth presently disclosed embodiments, other embodiments are also contemplated, for example, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
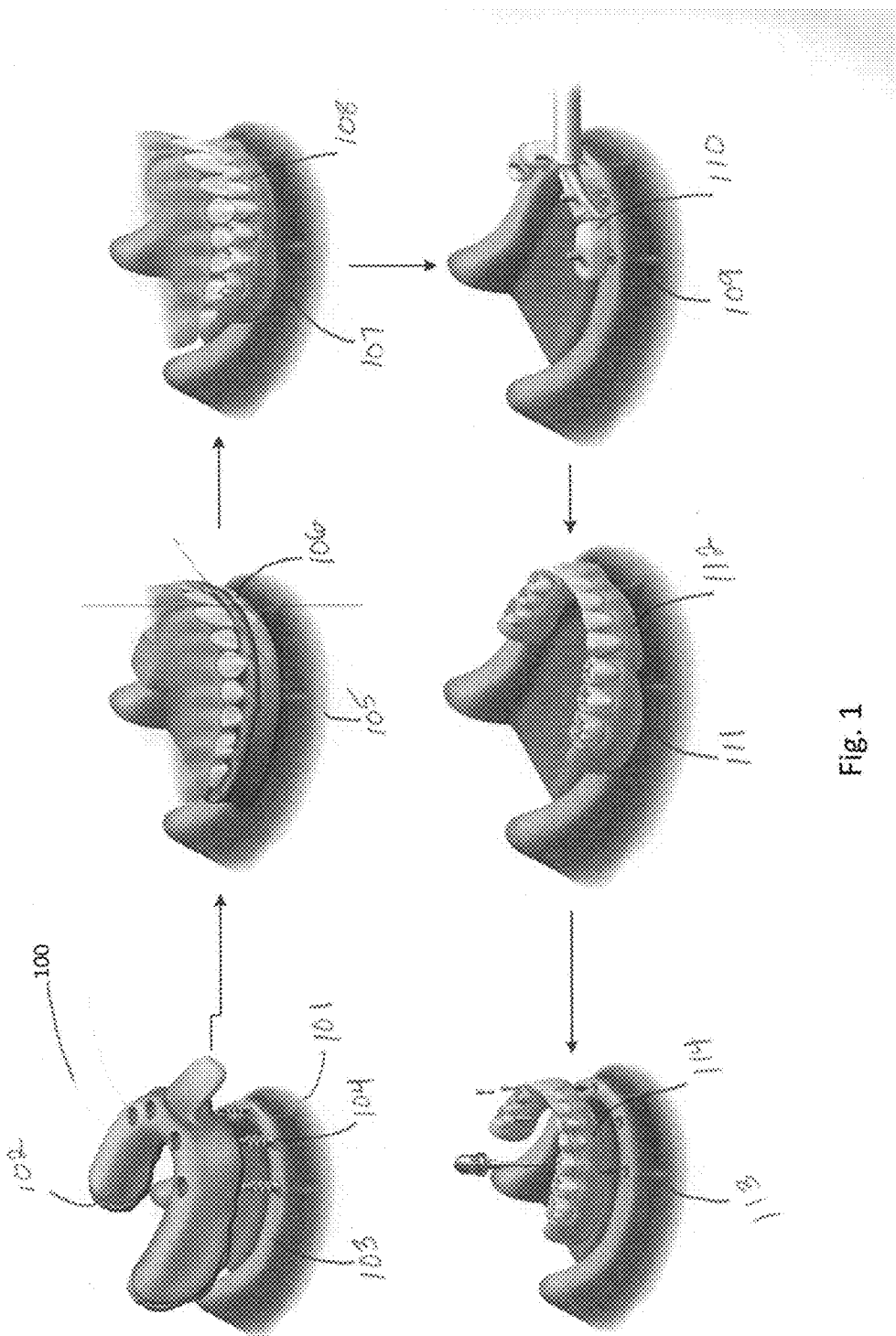
FIG. 1 shows a conventional method of fabricating an implant-supported denture.

FIG. 1 illustrates conventional processes (100) for making implant-supported denture devices requiring physical impressions and multiple appointments between a dentist and patient. As illustrated in FIG. 1, a first appointment (101) is required for taking a preliminary physical impression (102) of the anatomy (103) of an edentulous patient in which implants (104) have been installed. A second appointment (105) is required for obtaining jaw relationship records (106) and shade selection. In a third appointment (107), the patient is evaluated for a trial denture set-up try-in (108). A fourth appointment (109) may be required for a verification jig (110) try-in, and a final impression is taken. In a fifth appointment (111), the denture set-up and substructure framework (112) is tried-in and evaluated by the dentist. At the sixth appointment (113), the final denture prosthesis (114) may be installed.

A method for making implant-supported denture devices without physical impressions is provided. Methods provided herein, exemplified in FIG. 2a and FIG. 2b, result in a reduction in the number of appointments needed by the conventional processes described in FIG. 1, without decreasing quality of the final denture.

Figure 2A:
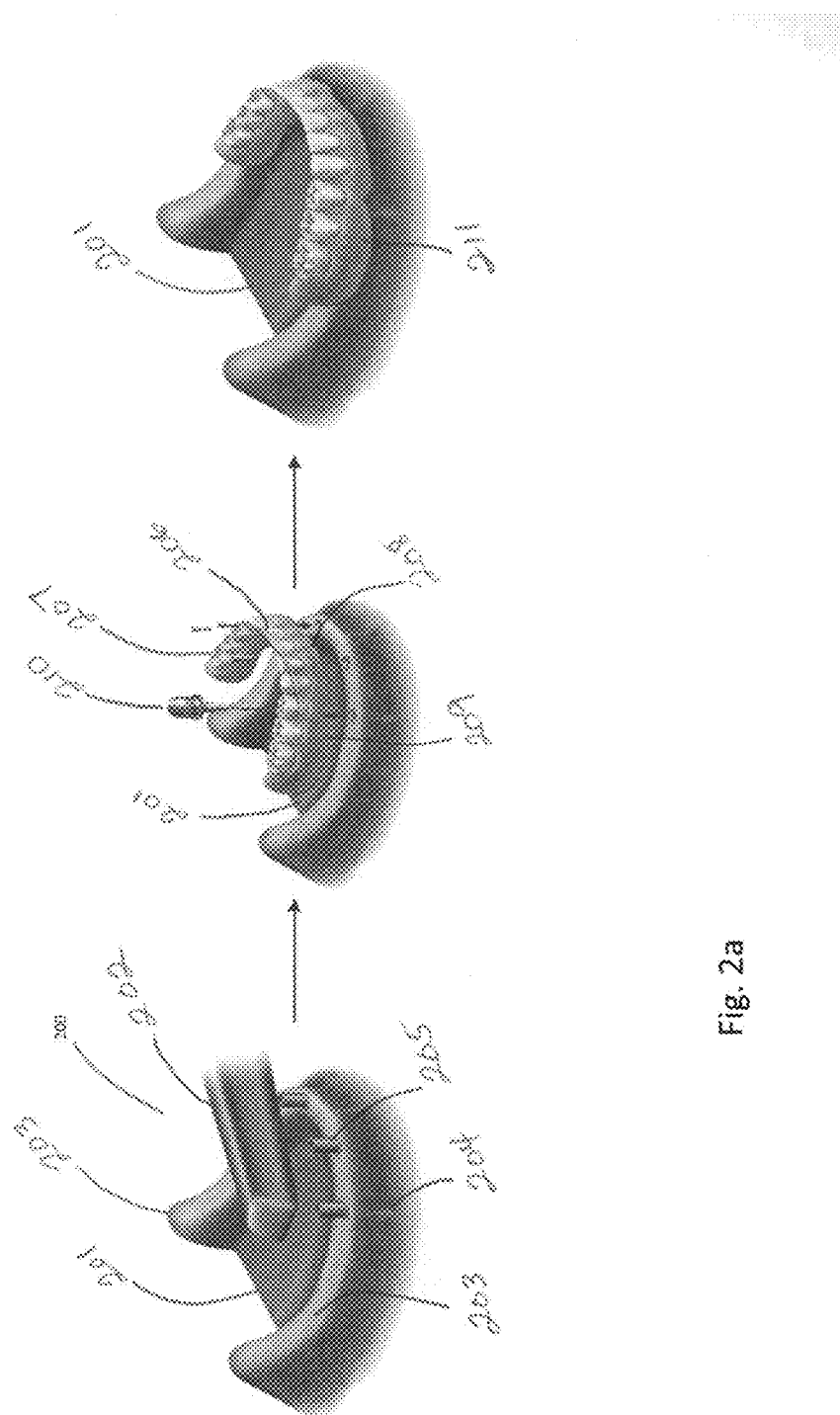
FIGS. 2a and 2b show embodiments of methods of making implant-supported denture as described herein.
Figure 2B:
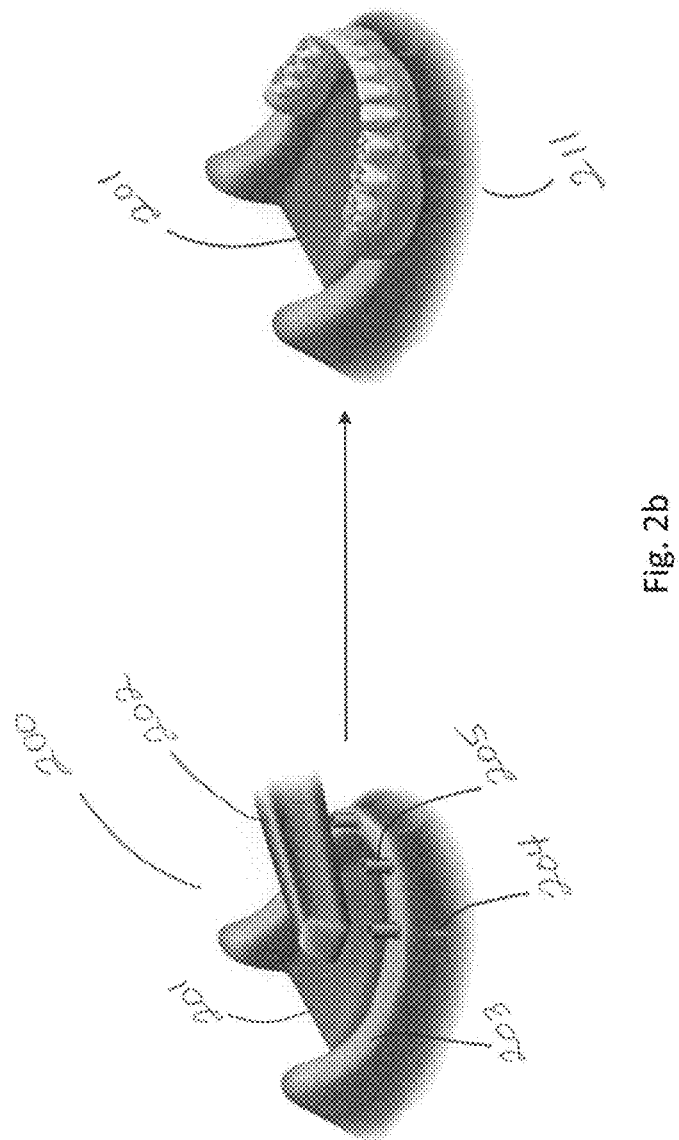

Methods for making implant-supported denture devices according to embodiments of the processes described herein are illustrated in FIG. 2a and FIG. 2b. As illustrated in FIGS. 2a, and 2b, a method (200) is provided wherein a first appointment digital impressions are obtained by scanning the oral cavity (201) of a patient with a scanning device (202), oral structures (203) and the implant (204) positions as indicated by digital impression copings (205). The digital impressions are taken in the doctor's office, and a denture design and supporting substructure design may be designed by the dentist or dental laboratory using a dental CAD program. The substructure (206) may be milled from metal, and the denture shape may be printed on a 3D printer. In alternative embodiments, the substructure may be made through an additive fabrication process such as electron beam melting. The gingival portion of the denture may be milled rather than printed. The two pieces are combined, and a denture mold may be made from the assembly of the denture shape and the substructure. The printed denture shape is removed from the mold, and denture teeth (207) are put in the corresponding recesses and fixed to the substructure with wax or other fixation material (208), to form a try-in denture (209). In a second appointment as illustrated in FIG. 2a, the try-in denture (209) is attached to the implants with an attachment (210), and evaluated by the dentist for fit and aesthetics. The try-in denture is returned to the laboratory for processing into a final implant-supported denture (211), and in a subsequent appointment, the final prosthesis is installed. In one embodiment, exemplified in FIG. 2b, a final implant-supported denture (211) may be made and delivered to the patient without a try-in appointment.

Images

A method of making a digital impression or digital model of a patient's oral anatomy is provided. Images of a patient's oral anatomy and implant information are obtained to form digital impressions that are used in place of physical impressions.

A plurality of images may be acquired including occlusal, lingual and buccal images of the edentulous jaw that comprises implants, images of the edentulous jaw with and/or without digital impression copings attached to the implants, images of the opposing jaw, images of any dentition, and images of other oral structures. If available, images of a patient's existing denture devices may be acquired to obtain bite registration data to establish the occlusal relationship between maxillary and mandibular teeth. Existing denture devices may include temporary, interim or provisional implant-supported denture devices or removable denture devices, and may comprise fewer than all of the teeth that will be included in the final denture prosthesis. Oral structures may include hard and soft gingival tissue, and may include gingival and palatal characteristics.

Figures 3A, 3B:
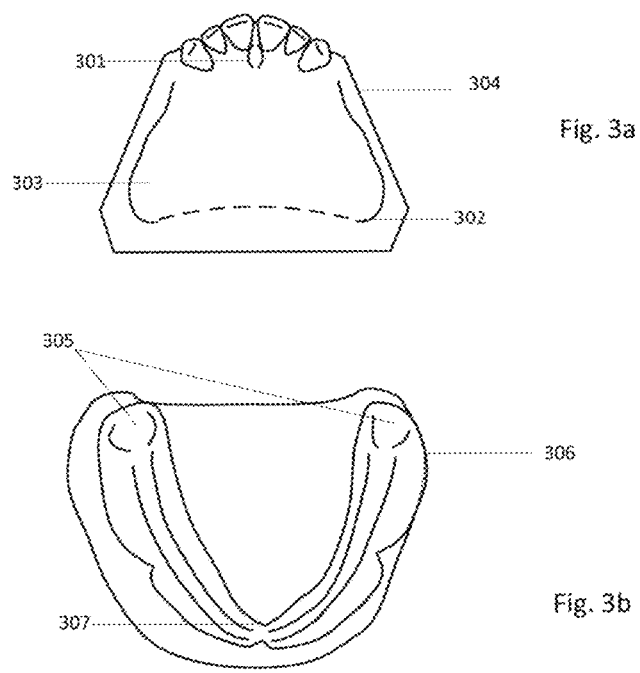
FIGS. 3a and 3b is a depiction of oral landmarks on maxillary and mandibular arches.

One or more oral structures may serve as oral landmarks for use in registering multiple images where the same oral landmark(s) is captured in more than one image. Anatomical structures suitable as oral landmarks include tissue that is sufficiently stable during the imaging process to provide consistency and precise identification of the landmarks in multiple images, allowing for better image registration. It has been found that some anatomical landmarks comprising thin gingival tissue may be more stable than areas having thicker tissue, such as gums, which may be more prone to flex and movement, for example, during intra-oral scanning. Anatomical oral landmarks, as depicted in FIGS. 3a and 3b, that are suitable for use herein may include incisive papillae (301), rugae, hamular notches (302), palatine raphe, and maxillary tuberosities (303), on the maxillary arch (304), and retromolar pads (305) and mandibular tori, on the mandibular arch (306), and labial and lingual frenum (307).

Dental Implants

Figure 4:
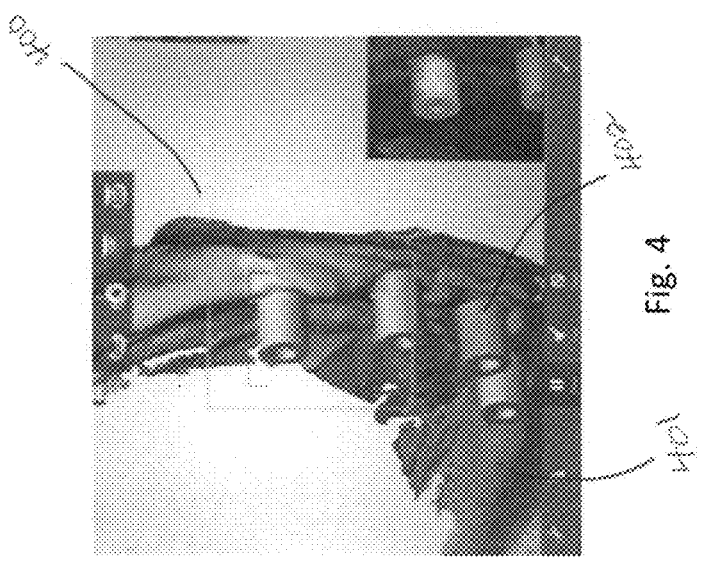
FIG. 4 shows an embodiment of an image of an edentulous jaw and digital impression copings.

As depicted in FIG. 4, to obtain information regarding the patient's implants, at least one image (400) is acquired of the edentulous jaw (401) in which implant digital impression copings (402) are attached to a plurality of implants in the patient's mouth. Digital impression copings capture the position and angulation of implants. In some embodiments, images of interim or provisional implant-supported dentures are obtained in position on the edentulous jaw. In embodiments where the provisional implant-supported denture device comprises only a portion of the teeth that will be used in a full denture, the provisional denture may be attached to only a portion of the implants, and digital impression copings may be attached to remaining implant sites. In this manner, the acquired image comprises image data of the provisional denture teeth and digital impression copings which may be used as landmarks to register multiple images.

Digital Impression Copings

Digital impression copings of known dimensions may be obtained that comprise flat, radius slot or other geometrically distinct feature or features for determining the implant position and angulation for a plurality of implants. Digital impression copings may removably engage with the plurality of implants for example, by a connection interface or counterpart feature on the connecting surfaces of the impression coping and implant. In one embodiment, the digital impression coping comprises a connection interface on a bottom surface that removably engages with a connection interface on the top surface of an implant. The digital impression coping may be affixed to the implant for example, by means of a screw or by friction retention, as described in U.S. patent application Ser. No. 12/800,784, entitled "Methods of Design and Fabricating Patient-Specific Restorations From Intra-Oral Scanning of a Digital Impression", which is incorporated by reference in its entirety, herein. Digital impression copings may comprise radiopaque material, or other material suitable for viewing by imaging techniques used to capture patient digital data.

Images and Imaging System

Images may be obtained by scanning devices, including hand-held intra-oral scanning devices, three-dimensional cameras, computed tomography or other imaging methods in place of physical impression media. Image data may be obtained and recorded by known methods for obtaining and recording patient information. The image data may be converted into digital datasets stored as files suitable for creating a computer generated 3D representation of the patient's oral anatomy.

A number of intra-oral scanners are available that are suitable for obtaining images of the patient's oral anatomy. Commercially available scanners include CEREC® (Sirona), Trios® (3Shape), and iTero™ (Cadent/Align Technologies, Inc.). A typical intra-oral scanning system (not shown) that is suitable for use with the methods for generating digital impressions include a base unit that serves as a housing for a microprocessor or computer, a scanning device, and a user interface, for example in the form of a touch screen. The scanning system may also include a user input device, for example, a stylus, keyboard or mouse that interfaces with the touch screen to allow the user to interact with the scanning system. The scanning device may include a wand with a probe having a profile and size that provides sufficient clinical access to obtain suitable intra-oral images of a patient to identify a preparation.

Digital impressions used to develop digital patient models for designing implant-supported restorations may require greater accuracy of the true dimensions of the patient's oral anatomy than conventional dental restorations. For example, alignment of teeth and substructures according to the position and orientation of implants may be important to achieve a final product with good fit for implant-supported restorations. Obtaining repeatable and accurate measurements of organic objects, such as anatomical oral structures, may also be challenging. Thus, in one embodiment, scanning systems that have low, consistent error rates with regard to accuracy and repeatability when imaging structures of a patient's oral anatomy is desired if multiple images are to be registered to create a digital three dimensional representation of the patient's oral situation.

In one embodiment, a method for acquiring image data of a patient having and edentulous jaw that has implants or abutments, comprises one or more of the following:
 a) acquiring an image of the edentulous jaw, and at least one oral landmark;
 b) acquiring an image of the edentulous jaw, an implant supported denture device attached to a portion of the implants or abutments, and digital impression copings attached to a portion of the implants or abutments;
 c) acquiring an image of the edentulous jaw, an opposing jaw that comprises dentition, for example, in the form of a provisional implant-supported denture device that is positioned on the opposing jaw, and the at least one oral landmark located on the edentulous jaw;
 d) acquiring an image of the edentulous jaw comprising digital impression copings connected to the implants or abutments, wherein the image includes image data of top and side surfaces of the digital impression copings, and which further comprises the at least one oral landmark located on the edentulous jaw;
 e) acquiring an image of the patient's removable or provisional upper denture where the image includes denture teeth and at least a portion of denture gingiva; and
 f) acquiring an image of the removable or provisional upper and lower dentures oriented in occlusion.

An example of dentition on an opposing jaw useful in obtaining bite-registration data may comprise, but is not limited to, natural teeth, a removable denture, or an implant-supported temporary or provisional denture. In one embodiment, removable or provisional dentures, may be scanned, for example, by a hand-held oral scanning device, or scanning the denture in a box scanner, such as a box scanner by 3Shape.

In another embodiment, a method for acquiring image data of a patient comprises the following method:
 a) acquiring scan data of an edentulous jaw of a patient having implants, a provisional implant-supported denture device attached to at least one implant of the edentulous jaw, and at least one oral landmark;
 b) acquiring scan data of a patient's dentition of the jaw opposing the edentulous jaw;
 c) acquiring scan data in the form of a bite scan capturing image data of both upper and lower jaws; and
 d) acquiring scan data of the edentulous jaws in which the implant-supported denture device has been removed after scanning, and digital impression copings attached to at least one of the implants.

In one embodiment, the edentulous jaw is a mandibular arch, and the at least one oral landmark is selected from a retromolar pad and a mandibular torus. In another embodiment, the edentulous jaw is a maxillary arch, and the at least one oral landmark is selected from a maxillary tuberosity, an incisive papilla, and a hamular notch.

Each image may be acquired, for example, in the form of a point cloud data set that is convertible to a 3D image for use in digital denture designing. Patient electronic images may be stored locally, or remotely, for example, in an .stl format, for use in the methods described herein. Images obtained in another format, such as 3Shape® .dcm file format, obtained by use of a 3Shape® scanning system, may be converted, for example, into an .stl file format. In one embodiment, a series of images, such as scans, are taken in the doctor's office, and image data is sent electronically to the laboratory via a network connection.

Registering Scans

Figure 5:
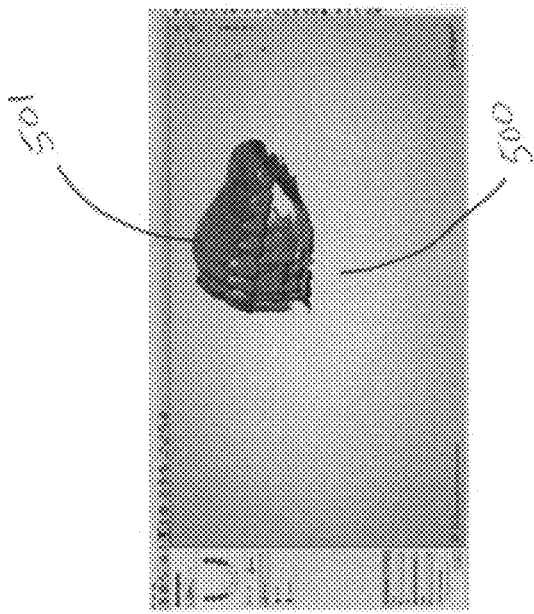
FIG. 5 shows an embodiment of registered images of a patient's oral anatomy and structures.

An imaging system (500) may be used to assemble the plurality of images into a digital model of the patient's oral situation as depicted in FIG. 5, at 501 using digital impression copings and/or oral landmarks as reference features. When registered, a plurality of images may provide a highly accurate, digital model from which to create a digital implant-supported denture design for use in the automated manufacture of an implant-supported denture device. Software programs are commercially available for aligning the plurality of images to form a digital impression or 3D model of a patient's oral anatomy. An example of commercially available software includes software by Geomagic, such as Geomagic® Control program (Geomagic, Research Triangle Park, N.C.), or 3Shape software programs.

In one embodiment, the images may be correlated using at least one common landmark as a reference point. The landmark may comprise an anatomical oral landmark or a digital impression coping, or dentition. In an embodiment, images are correlated using at least one anterior landmark and at least one posterior landmark. In a further embodiment, images are correlated with at least one anterior landmark and two posterior landmarks.

In one embodiment, three reference points are used to align a plurality of scans acquired of an edentulous jaw with and without an attached implant-supported denture device. In this embodiment, posterior landmarks may be selected from right and left digital impression copings, tuberosities, and retromolar pads, and dentition. Anterior landmarks may be selected from dentition, digital impression copings, facially-oriented papillae, and lingually-oriented papillae, such as the incisive papillae. Images of the edentulous jaw may be registered, for example, with images of a provisional denture device, such as a provisional implant-supported denture or a removable denture, in a bite-relationship to align teeth with implant positions, and provide teeth-to-implants relationships.

One method of making a digital model of a patient's oral anatomy for use in making an implant-supported denture device may comprise the step of acquiring a first image by scanning an edentulous jaw that comprises a provisional denture device attached to a plurality of implants, and a landmark; and acquiring a second image by scanning a portion of the patient's edentulous jaw that comprises digital impression copings connected to the plurality of implants wherein the provisional denture device has been removed, and a landmark, and wherein the first and second images comprise at least one landmark comprising an oral landmark or a digital impression coping that is common to each image; acquiring a third image of the edentulous jaw and the opposing jaw comprising dentition in a bite relationship; acquiring a fourth image by scanning upper and lower portions of the provisional denture device in a bite relationship; and registering the first, second, third and fourth images by aligning the images by common landmarks to form a digital model of the patient's oral anatomy. The digital model of the patient may be used to design the digital denture design, for example, by incorporating digital denture teeth, and optionally digital gingiva. The digital model of the patient may also be used to design a digital substructure.

Digital Design

Suitable computer programs for designing denture restorations include CAD programs that use the implants' special relation to the patient's oral anatomy to design patient-specific implant-supported denture devices, and that create output files suitable for use by automated manufacturing processes. Examples of which include software programs, such as 3Shape dental design software programs.

A dental CAD program may also be used to design a digital substructure design that is suitable for use in making the substructure by automated manufacturing processes. In one embodiment, intra-oral scan data is used as a reference when designing the substructure in a dental CAD program.

Figure 7:
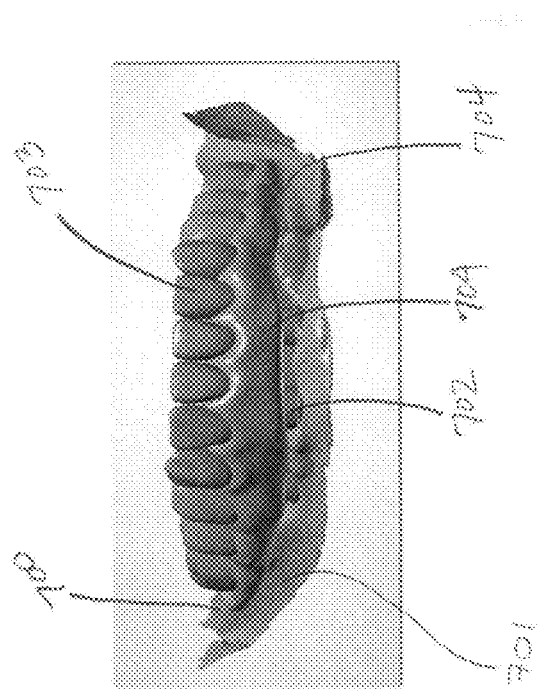
FIG. 7 shows one embodiment of the formation of a digital model.
Figure 6:
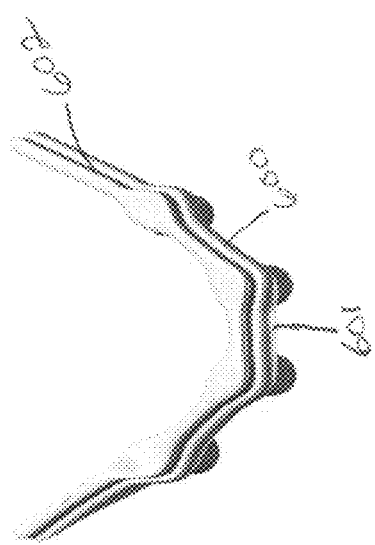
FIG. 6 shows an embodiment of a digital model of a substructure design.

A method for making a digital substructure design (for example, 600, at FIG. 6) is provided as follows. A digital model of a patient's edentulous jaw having digital impression copings attached to implant sites, as depicted in FIG. 7 at 700, is obtained after registration of a plurality of scans. Images containing digital impression copings are digitally modified to remove the digital impression copings from the image of the edentulous jaw. The edentulous jaw (701) may be aligned with an image of the opposing jaw (not shown) to provide alignment. A digital substructure (702) or bar is designed on the digital jaw (701) to accommodate the size, position and orientation of the implants, as well as the patient's oral anatomy.

Digital Design of Denture

A digital model used in the design of the substructure may also be used to provide the basis of a digital denture design that will be used to form the implant-supported denture device by automated processes.

Figure 8B:
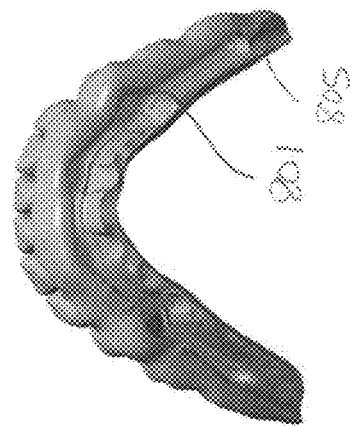
FIGS. 8a and 8b show a digital model of a denture design.
Figure 8A:
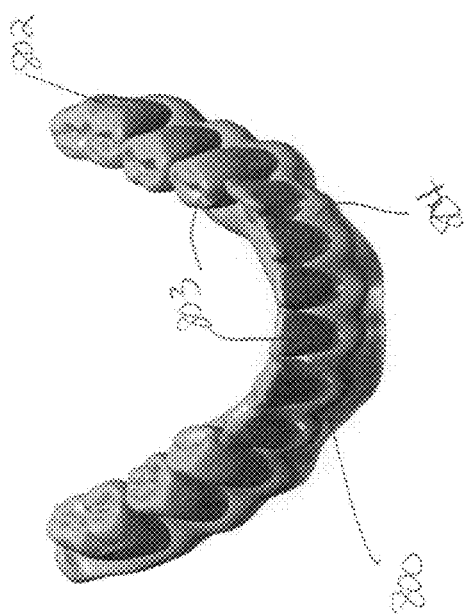

In one embodiment, as exemplified in FIG. 7, a digital model of the edentulous jaw (700) comprising a digital substructure (702) is obtained for use in designing the digital denture design (704, 800). Digital gingiva (704) and digital denture teeth (703), obtained from a digital library of teeth, are designed over the digital model of the substructure (702) to align teeth position with digital implant sites on the substructure. Once aligned, the digital denture design depicted in FIGS. 8*a* and 8*b* (800) is digitally separated from the digital substructure design. In one embodiment, the digital denture design comprises a digital mating cavity (801) corresponding to the dimensions of the digital substructure (600). In this embodiment, the digital denture design comprises an upper side (802) that comprises digital denture teeth (803) and digital gingiva regions (804), and a lower side (805) that comprises a digital mating cavity (801) corresponding to the digital substructure.

In one embodiment the digital substructure is subtracted from a digital denture design to form the digital mating cavity that corresponds with the dimensions of a digital substructure.

In another embodiment, the digital substructure scan may be merged to the scan of the digital denture design, and the merged substructure scan is then subtracted or separated from the digital denture design with a Boolean operation to ultimately produce a denture shape with a mating cavity that fits intimately with the substructure.

In another embodiment, the digital substructure design is modified to remove any undercut features or notches (601 or 602), prior to designing the digital denture shape. Undercuts or notches appearing in the digital substructure may be reproduced in a digital denture shape that is designed around it, and then may be reproduced in the denture shape formed by automated processes. The undercut features reproduced in the denture shape may hinder the assembly of the actual substructure and denture shape. Thus, in one embodiment, a digital denture is designed around a modified digital substructure design in which the undercuts have been digitally removed, thereby providing a digital denture shape having a mating cavity lacking undercut features present in the digital substructure design. When reproduced in a physical form by automated manufacturing processes, the substructure can easily be removed from the mating cavity of a denture shape which may otherwise be restricted if the undercut features were incorporated into the denture shape design.

Figure 9:
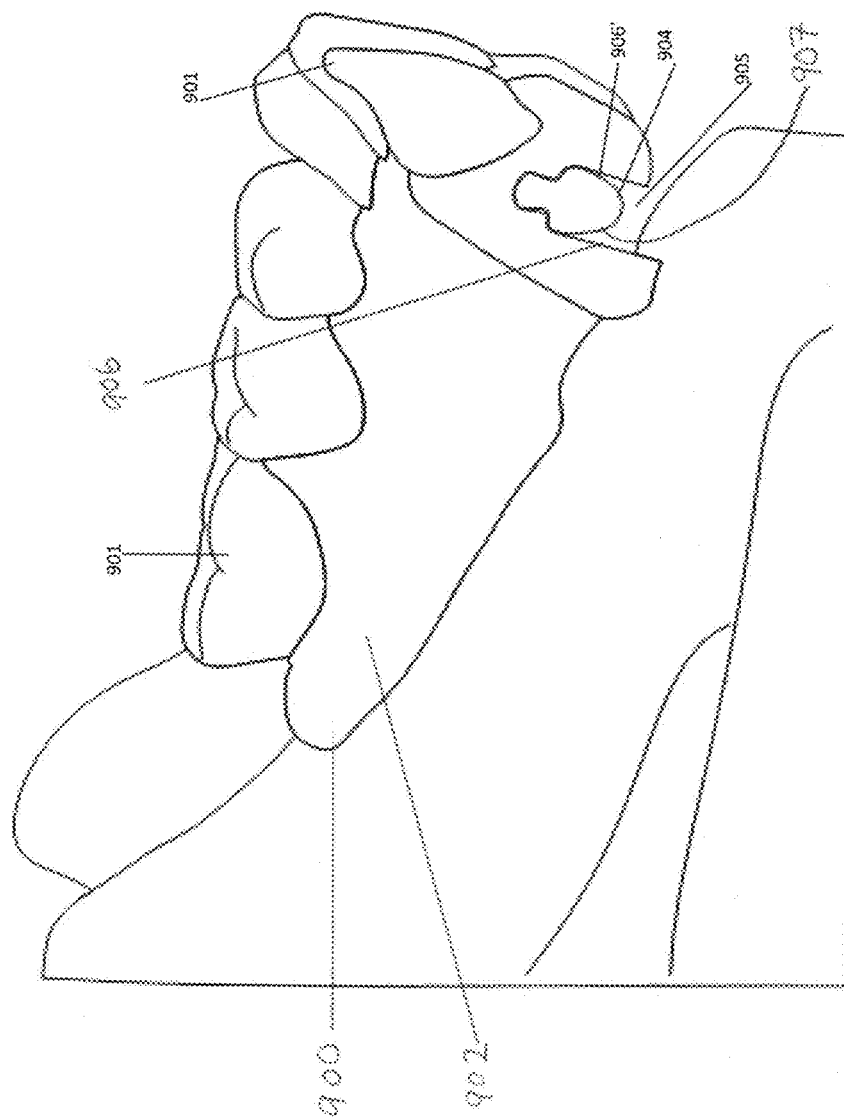
FIG. 9 shows a cross-sectional representation of a portion of a digital design.

FIG. 9 depicts a cross-sectional representation of an embodiment of a digital denture design (900) comprising digital denture teeth (901) and digital gingival (902). A cross-sectional portion of the digital substructure (904) is seen in the digital mating cavity (905) of the digital denture design (900). In one embodiment, as depicted in FIG. 9, the digital mating cavity (905) is defined by a buccally-oriented wall (906') and a lingually-oriented wall (906) that is designed without the undercut features (907) of the digital substructure.

A denture shape formed comprising the digital mating cavity will have a physical space for receiving the physical substructure in a specific alignment in accordance with the digital model and implant positions. Once assembled, the configuration enables proper positioning of the denture teeth relative to the bar and implants so that the teeth occlude properly with opposing teeth.

In one embodiment, the digital denture teeth used in the digital denture design correspond to teeth provided in the provisional denture. Digital teeth may be selected from a digital library of a computer software program for designing dental restorations. The library may comprise teeth having specific size, form, shape and color that are available from known manufacturers of denture teeth. Actual denture teeth may be indicated by a mold number providing consistency in size and form, corresponding denture teeth designs. Examples of denture teeth include Kenson® denture teeth (distributed by Myerson LLC, Chicago, Ill.) or VITA Vident® denture teeth (Vident, Brea, Calif.).

A method for making a digital denture design for use in manufacturing an implant-supported denture device is provided. In one embodiment, the method for making the digital denture design comprises the following steps:
a) acquiring scan data of an edentulous jaw of a patient having implants, a provisional denture device attached to at least one implant of the edentulous jaw, at least one digital impression coping attached to at least one implant, and at least one oral landmark;
b) acquiring scan data of a patient's dentition of the jaw opposing the edentulous jaw;
c) acquiring scan data of both upper and lower jaws in bite registration; and
d) acquiring scan data of the edentulous jaws in which the provisional denture device has been removed after scanning, and digital impression copings attached to at least one of the implants;
f) identifying at least one oral landmark that is present in the acquired scans as a reference point;
g) registering a plurality of the scans by at least one reference point to obtain a digital model of the patient's oral anatomy;
g) generating a digital substructure design to accommodate the digital model of the patient's oral anatomy; and
h) generating a digital denture design that comprises digital denture teeth and digital gingiva on an upper side and a digital mating cavity corresponding to the digital substructure on a lower side.

In one embodiment, the method comprises subtracting digital data that corresponds to the dimensions of the digital substructure design from the digital denture design to form a digital denture design having a mating cavity for receiving a substructure.

Automated Manufacturing Processes for Denture Shape and Substrate

CAD design used in conjunction with computer-assisted manufacturing (CAM) may be used to form the denture shape and/or substructure, based on the digital design for each. The resulting denture shape and/or substructure combine detailed characteristics of the patient's oral anatomy and precise implant information, as obtained from the digital data. Gingival features and palatal contours unique to the patient as well as information regarding the position and orientation of the implants may be faithfully replicated from the digital denture and substructure designs. As such, the objects created are uniquely tailored to match both the implants and the patient's oral anatomy. An implant-supported denture device, formed from design made by CAD techniques that incorporate patient specific information and precise implant information, has a custom fit which is important to providing a secure fit.

Automated manufacturing processes suitable for use in the described methods described include both subtractive and additive automated manufacturing processes. Additive processes suitable for use in manufacturing a denture shape include those known by terms such as three-dimensional (3D) printing, additive manufacturing, rapid prototyping and rapid manufacturing. Other additive processes comprise laser sintering, such as selective laser sintering, electron beam sintering, and fused deposition modeling. In one embodiment, the substructure is also made by an additive manufacturing process.

Figure 10B:
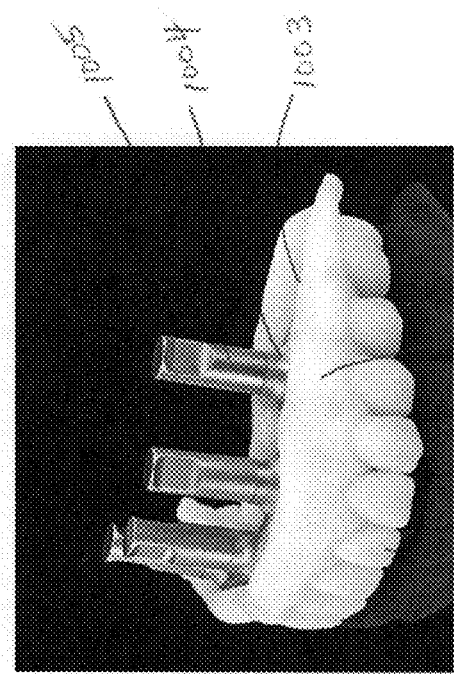
FIGS. 10a and 10b show embodiments of a printed denture shape with a substructure.
Figure 10A:
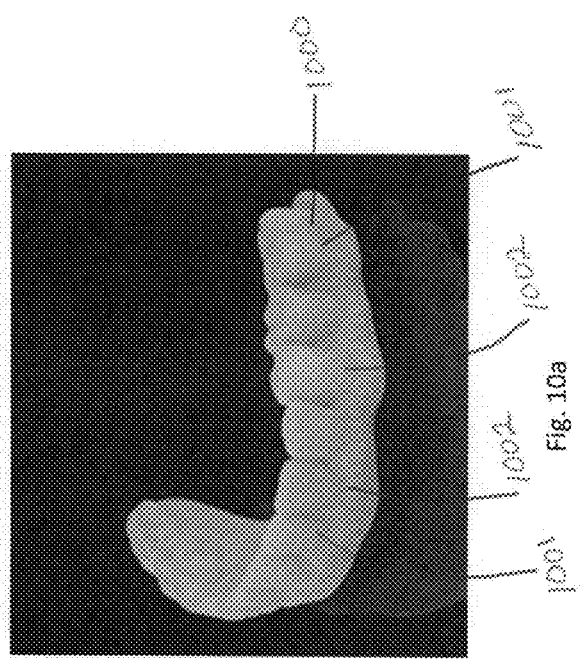

FIGS. 10 and 10*b* exemplify one embodiment comprising a denture shape (1000) made by a 3D printing process. A denture shape (1000) may be made that fits on the lower edentulous ridge of a patient. In one embodiment, the printed denture shape comprises printed features replicating features of the digital denture design. The printed denture shape comprises a printed lower arch, printed anterior and posterior teeth regions (1001) and surrounding gingival regions (1002), and a mating cavity (1003) for placement of the substructure (1004) for attachment with the implants. In one embodiment, a lower printed denture shape (1000) comprises a printed base that fits securely to mandible of a patient. In another embodiment, an upper printed denture shape is provided for fitting on the maxillae of a patient, and may comprise a printed upper arch that comprises printed anterior and posterior teeth regions and surrounding gingival regions, and a printed palate region that fits securely to the top of a patient's mouth.

In one embodiment, a 3D printing process used to create a denture shape or substructure from a digital design, comprises depositing material in a pattern corresponding to a cross-sectional layer of the digital design. Material which is sufficiently flowable, either as a liquid, or a solid that can be rendered flowable, may be formed layer by layer by a 3D printer. The flowable material is solidified and subsequent layers are formed thereon. Each layer corresponds to a cross-section of the virtual representation and a cross-section of the object to be formed. Cross-sections of the digital design are used to form each layer, for example, by moving a print head over a work piece and activating elements of the print head to create a layer of the object. Printing may be performed by any method known in the art to form layers that ultimately result in a solid object.

Polymeric materials suitable for use herein include but are not limited to polyamides, polyesters, polyolefins, polyimides, polyacrylates, polyurethanes, vinyl esters, or epoxy-based materials. Other polymeric materials include styrenes, styrene acrylonitriles, acrylonitrile butadiene styrene (ABS) polymers, polysulfones, polyacetals, polycarbonates, polyphenylene sulfides and the like. In one embodiment, polymeric materials include those based on acrylic and methacrylic monomers. In another embodiment, polymers suitable for use herein include but are not limited to acrylonitrile butadiene styrene (ABS), polycarbonate (PC), polylactic acid (PLA), high density polyethylene (HDPE), PC/ABS, and polyphenylsulfone (PPSU).

In another method, powder is used, instead of liquid, to form the three-dimensional (3D) object. Powder applied to a substrate in a pattern corresponding to a layer of a digital representation, may be hardened by any known method suitable for the selected powder such as heating. Each layer of a 3D object may be created by spreading a thin layer of powder over the surface of a powder bed and hardening, or partially hardening, the powder as each layer is laid down. Subsequent layers of powder are laid down in sequence upon coalescing of the initial layer to a stable form. Whether liquid or powder, material deposition is controlled by a computing device, such as a computing-system, computer, personal computer, microcontroller, or the like. Examples of suitable 3D printing devices include 3D printers manufactured by 3D Systems (Valencia, Calif.) and Stratasys (Minneapolis, Minn.)

Figure 11:
FIG. 11 shows an embodiment of a substructure.

Additive manufacturing processes, such as 3D printing, are distinct from subtractive processes. Examples of subtractive techniques suitable for use in methods described herein include known machining or milling techniques that rely on removal of material by cutting or drilling (a subtractive process). FIG. 11 depicts an embodiment of a substructure (1100) that has been milled by an automated manufacturing process.

In one embodiment, the automated manufacturing device may be connected directly to a computing system used to design the digital denture design. Alternatively, the automated manufacturing device may be connected to a remote computer by a network interface that receives a data file corresponding to the digital denture design. For example, a 3D printing system may comprise a computing device, a 3D printer having a printer controller and a 3D print head module. The 3D printer may include a buffer memory for receiving a print file in the form of signals from the computing device, an image buffer for storing printing data, and a printer controller that controls the overall operation of the 3D printer. The printer controller may control, for example, one or more printer drivers for driving the 3D print head module and associated transport mechanisms. A data store in the form of a local memory and a display unit for setting the parameters of the printer may also be included.

In one embodiment, a method is provided that comprises the step of configuring an automated manufacturing sequence based on a digital denture design made by CAD design, and manufacturing a denture shape based on the automated manufacturing sequence. In a further embodiment, a method comprises the step of configuring an automated manufacturing sequence based on the digital substructure design made by CAD design, and manufacturing the substructure based on the automated manufacturing sequence.

Figure 12:
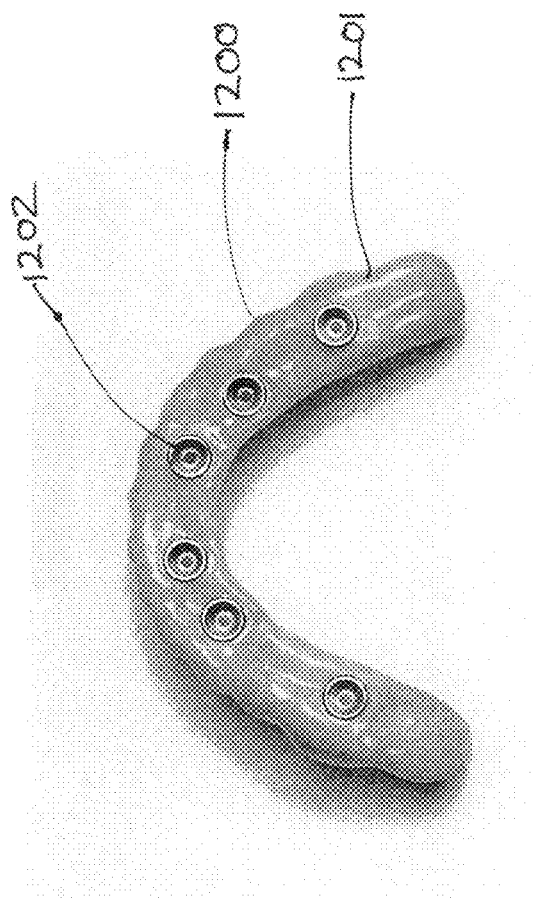
FIG. 12 shows an embodiment of an implant-supported denture device.

In one embodiment, a denture shape may be made by an automated manufacturing process with a material that does not require a separate substructure. In one embodiment, as depicted in top-down view of FIG. 12, the implant-supported denture device (1200) may comprise a monolithic component that comprises denture teeth regions (not shown) and denture gingiva (1201) regions wherein the monolithic component attaches directly to the implants at attachment points (1202). Materials suitable for use as the monolithic component include, but are not limited to, ceramic materials, such as zirconia. In one embodiment, an implant-supported denture device comprises a denture shape milled from zirconia, and does not have a supporting substructure.

Forming a Mold of Denture Shape

In a further embodiment, a printed denture shape and/or a substructure may be assembled directly as an implant-supported denture device, such as a try-in, temporary or final denture device without further processing.

Figure 13:
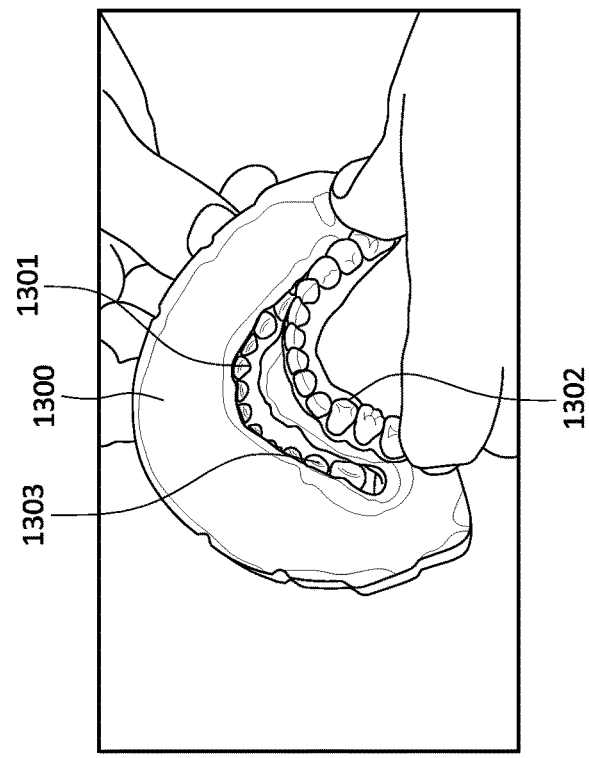
FIG. 13 shows an embodiment of a mold and a denture shape.

In other embodiments, the printed denture shape and, optionally, substructure, may be used in further manufacturing steps for making an implant-supported device. As illustrated in FIG. 13, a mold (1300) is provided that comprises an impression (1301) of the denture shape (1302), and comprises recesses (1303) for setting actual denture teeth. Traditional mold-forming techniques and materials known in the dental industry for making molds or dental impressions may be used in the processes described herein. By way of example, and not by limitation, materials suitable for making the mold include sodium alginate, rubber, stone, hydrocolloid, polyether and silicones including condensation cured silicones and addition-cured silicones, including polyvinyl siloxane (PVS).

In one embodiment, the method of forming a denture mold comprises acquiring an assembly comprising a denture shape and substructure. The denture shape comprises a mating cavity for receiving the substructure, and the substructure is set in the mating cavity, as shown in FIG. 10b. In one embodiment, the assembly comprises a holder for holding the substructure, and the substructure is optionally removably attached to the holder and positioned in the mating cavity of the denture shape. The method of making the mold further comprises making a physical impression of the assembly in a formable material, and removing the assembly from the formable material. In one embodiment, a mold is made by pouring formable material around the assembly that is set in a secondary container; in another embodiment, the mold may be made by pressing a formable material onto the assembly. The formable material may be hardened prior to removing the assembly from the mold, without compromising the impressed details on the mold material.

Figure 14:
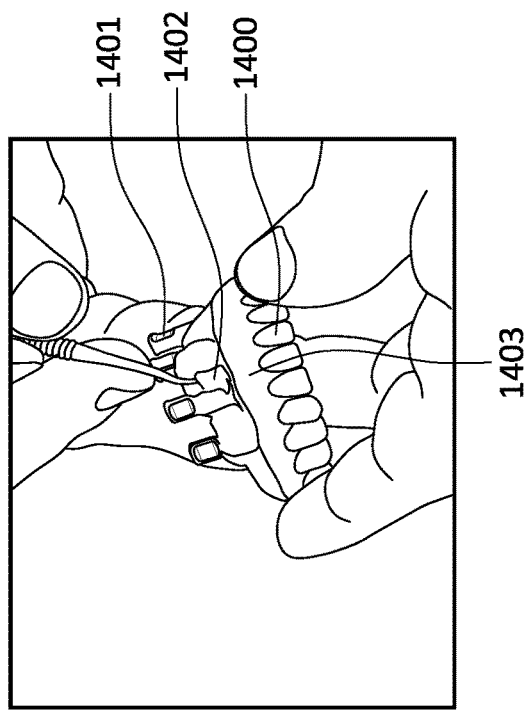
FIG. 14 shows an embodiment of a denture shape and substructure with block-out material.

In a further embodiment, as seen in FIG. 10, replicas (1005) are attached to the substructure for masking the connection to the implant during mold making or preparation of a denture device. As exemplified in FIG. 14, the assembly (1400) may further comprises replicas (1401) attached to the substructure (not visible) and block-out material (1402) applied to the denture shape (1403) and substructure, for example, to keep mold material out of the space. The block-out material may comprise wax, or other material suitable for keep mold material out of the space, and that is removable from the assembly after formation of the mold. Thus, methods of forming a denture mold may further comprise one or more of the steps of attaching replicas to the assembly to block the implant openings of the substructure, and applying a mold block-out material to the assembly.

A denture mold made by methods described herein may replicate or capture the exact position, size, occlusal scheme, and alignment of the teeth as provided by the digital denture design, assuring proper alignment with the implants. In one embodiment, the mold replicates gingival features created in the denture shape thus, providing a more realistic appearance and minimizing manual processes to create natural features.

Forming a Try-in, Temporary or Final Denture

A try-in denture is formed that comprises pre-formed denture teeth that correspond in size and shape to the digital denture teeth incorporated into the digital denture design, and which are replicated in the 3D-printed denture shape. The pre-formed denture teeth may also be used in the final implant-supported denture. Denture teeth may comprise teeth corresponding to specific mold numbers as provided for by the denture teeth manufacturer, such as Kenson® denture teeth (distributed by Myerson LLC, Chicago, Ill.) or VITA Vident® denture teeth (Vident, Brea, Calif.).

Figure 15B:
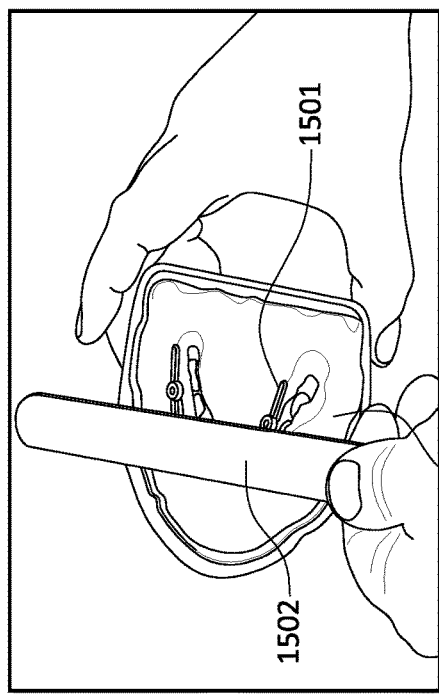
FIGS. 15a, 15b and 15c show an embodiment of a process for forming an implant-supported denture device.
Figure 16:
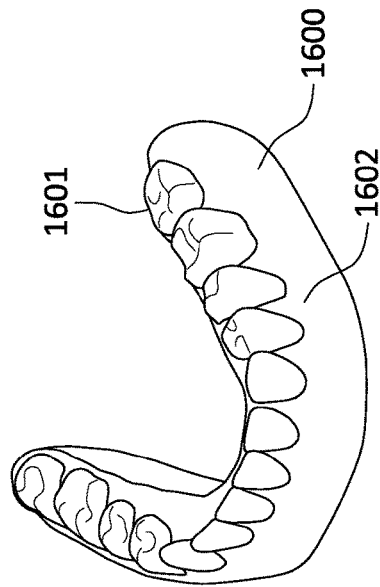
FIG. 16 shows an implant-supported denture try-in device.
Figure 15A:
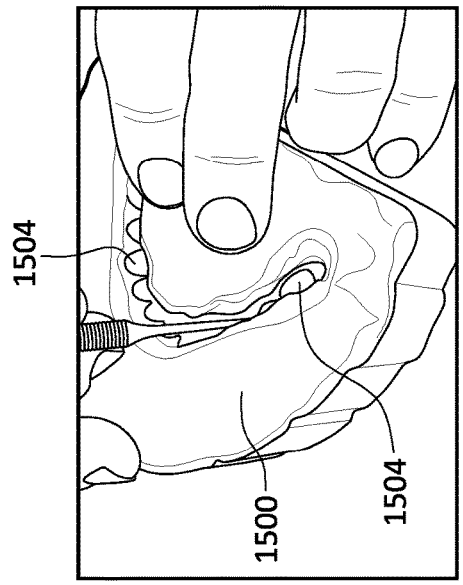
Figure 15C:
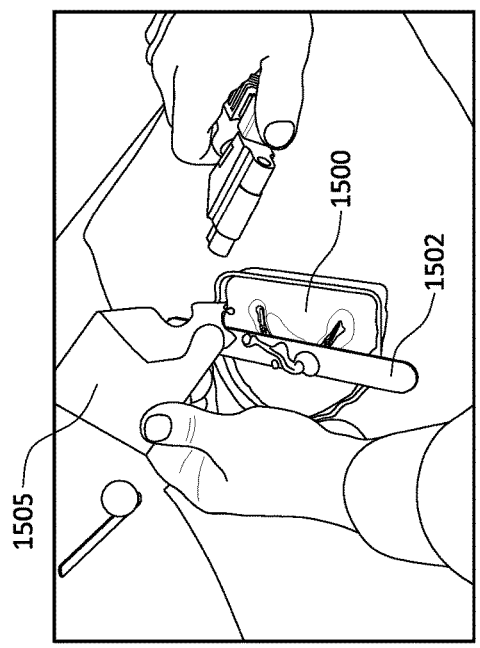

In one embodiment, an implant-supported denture device, such as a try-in denture is made by placing pre-formed denture teeth into recesses (1504) of the mold (1500) as shown in FIG. 15a. In one embodiment, depicted in FIGS. 15b and 15c, a substructure (1501) optionally attached to a holder (1502), is placed into the mold (1500), and affixed to denture teeth (1503) that have been set in mold recesses (1504) by a fixation material (1505). The fixation material may be any material suitable for attaching the denture teeth to the substructure. Fixation material includes material that may be rendered deformable so that adjustments to the position of the denture teeth relative to the substructure may be made, for example, by the dentist or dental laboratory. In one embodiment, molten wax is added to the mold to affix the denture teeth and the substructure, forming a try-in denture. FIG. 16 shows an embodiment of a completed try-in denture (1600) comprising actual denture teeth (1601), a gingival region (1602) made from the fixation material, and a substructure (not shown).

Thus, one method for forming a denture device, such as a try-in denture, a temporary denture, or a final denture comprises the steps of acquiring a denture mold of a printed denture shape; setting denture teeth in recesses in the mold; providing a substructure; and affixing the denture teeth to the substructure by a fixation material.

Forming a Final Denture

After evaluation and optional adjustments by a dentist or dental laboratory, a final denture maybe formed. In one embodiment, a process for forming a final denture comprises placing the try-in denture to the mold, aligning the denture teeth into mold recesses; removing the deformable try-in fixation material; and introducing a final denture restoration fixation material such as an acrylic securely attaching the denture teeth to the substrate. The final denture gingiva regions may be formed in the mold, and milled into final shape, or incorporated by traditional denture making techniques.

One method of making an implant-supported denture device is provided, wherein the implant-supported denture device comprises a try-in denture, a temporary denture, or a permanent denture. The method for making the implant-supported denture device may comprise the steps of:
a) acquiring an assembly that comprises i. an implant-supported denture shape made by an automated manufacturing process that comprises a mating cavity for receiving a substructure, and ii. a substructure positioned in the mating cavity of the denture shape;
b) forming a mold of the assembly;
c) separating the assembly from the mold;
d) inserting denture teeth into recesses in the mold;
e) placing the substructure in the mold; and
f) introducing a fixation material into the mold to affix the denture teeth to the substructure to form an implant-supported denture device.

FIG. 17 is a block diagram of one method (1700) of making an implant-supported denture device for a patient comprising at least some of the following steps:
a) attaching a digital impression coping to a plurality of dental implants (1701) implanted in a patient's oral cavity;
b) scanning the patient's oral cavity (1702) to acquire a plurality of images of the edentulous jaw, oral landmarks, digital impression copings, and optionally, a provisional denture device and an opposing jaw;
c) saving the images into an electronic storage medium;
d) registering a plurality of images (1703) by aligning at least one oral landmark in common on more than one image;
e) creating a digital denture design and a digital substructure design (1704) based on the acquired images;
f) manufacturing a denture shape (1708) and a substructure (1709) using an automated manufacturing process based on the digital denture design and the digital substructure design;
g) assembling the denture shape and the substructure (1705);
h) forming a denture mold (1706) from the assembly;
i) removing the denture shape and the substructure from the denture mold;
j) inserting denture teeth into recesses (1710) formed in the denture mold;
k) inserting the substructure into the denture mold (1711); and
k) fabricating the implant-supported denture device (1707, 1712) that is attachable to the implants by introducing a material into the denture mold to affix the denture teeth to the substructure.

Figure 18:
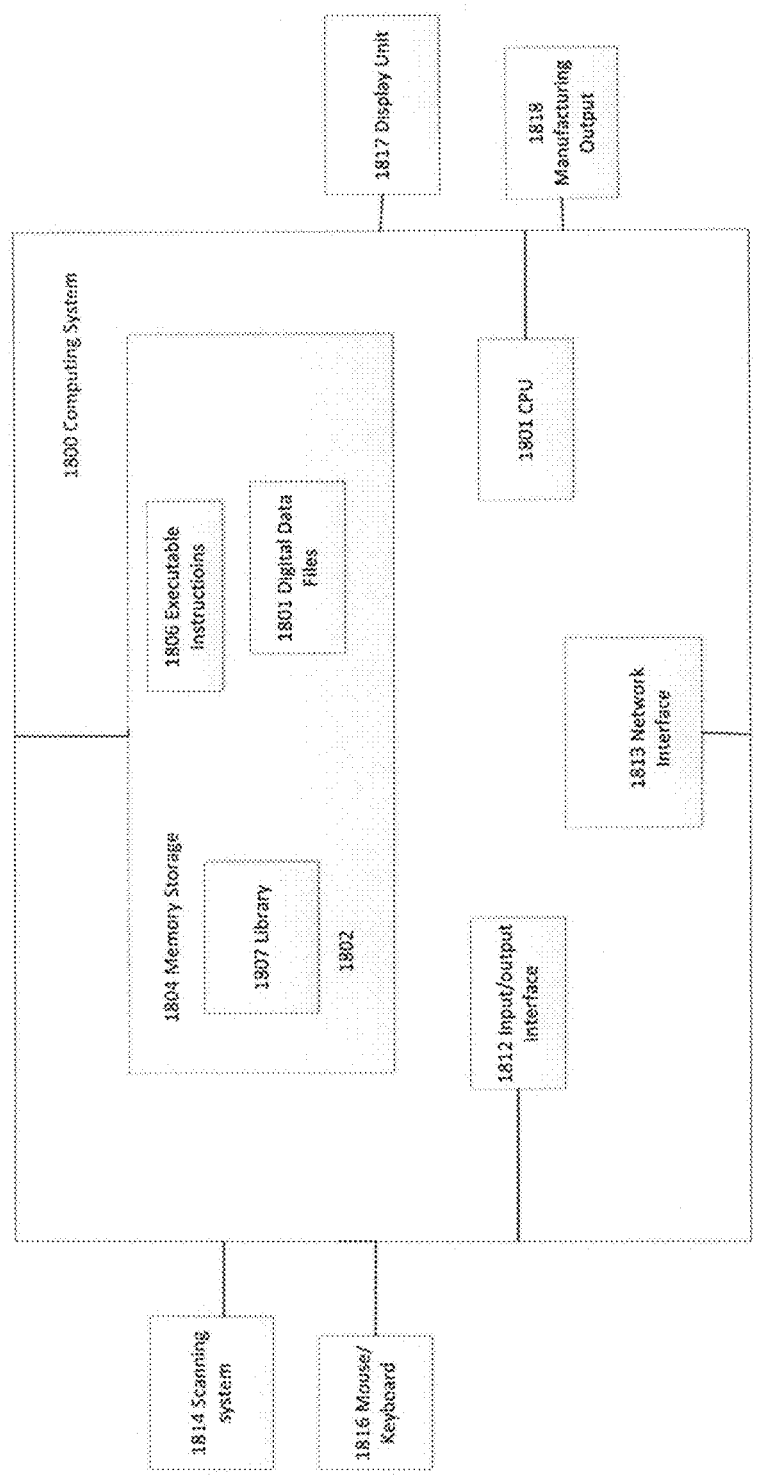
FIG. 18 shows a computing system of an embodiment described herein.

Computer Architecture:

FIG. 18 exemplifies a computing system that is suitable for use in performing some or all aspects of the methods according to the flow diagram of FIG. 18. A computing system (1800) may include a central processing unit (CPU) (1801), and a system memory (1802). The computer may further include a memory storage device (1804) for storing one or more programs (1806) and a database, such as a library or files (1807). Programs (1806) stored in the memory storage device may include instructions for use in completing tasks described by modules represented by flow diagrams of FIG. 17 (for example, blocks 1702-1704, and 1708-1709). The memory storage device (1804) and its associated computer-storage media may provide non-volatile storage for the computing system (1800). Although the description of the computer-storage media contained herein refers to a memory storage device, such as a hard disk or CD-ROM, it should be appreciated by those skilled in the art that computer-storage media can be any available storage media that can be accessed by the computing system (1800). Computer-storage media may include volatile and non-volatile, removable, and non-removable media implemented in any method or technology for the non-transitory storage of information such as computer-storage instructions, data structures, program modules, or other data. For example, computer-storage media includes but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage devices, or any other medium which can be used to store the desired information and which can be accessed by the computer.

The computing-system (1800) may also include an input/output controller (1812) for receiving and processing input from a number of input devices (not shown) including a keyboard, a mouse, and a touch screen. Similarly, the input/output controller (1812) may provide output to a display or other type of output device. For example, steps of designing the digital patient model by registering scans may be performed wherein the scans are displayed on a display or other output device, and an input controller receives input from an input device such as a mouse that is operated by a user receiving and processing input to register the scans.

Computer executable instructions in the form of a software program stored on the memory storage device for registering the scans may be implemented by the user via the user interface or input devices. In another embodiment, the steps of designing the digital substructure and digital denture design may be performed wherein the digital patient model and/or scans are displayed on a display or other output device, and a computer-executable program for designing the digital designs that may be stored on the memory storage device is implemented by the user via an input device, whereby the input controller receives and processes input from the input device to design the digital substructure and digital denture. Digital files containing, for example, the scans, the digital patient model or digital designs for use in automated manufacturing may be stored on the memory storage device, or stored locally on other computers attached to the computing system.

A bus may enable the CPU (1801) to read code and/or data to/from the memory storage device (1804) or other computer-storage media. The program modules (1806) may include software instructions that, when loaded into the processing unit (1801) and executed, cause the computing-system (1800) to perform method steps described herein. The program modules (1806) may also provide tools or techniques by which the computing-system (1800) may participate within the overall systems or operating environments using the components, flows, and data structures discussed throughout this description.

A system for fabricating an implant-supported denture device is provided that comprises
 a) a digital image scanning device that acquires a plurality of digital images of a patient's oral cavity that comprises a plurality of implants, digital impression copings that indicate the orientation of the implants, and at least one oral landmark as a reference;
 b) a computing system comprising computer-executable instructions for
  registering the plurality of digital images to form a digital patient model using the at least one oral landmark;
  generating a digital denture design and a digital substructure based on the digital patient model; and
  separating digital data that corresponds with the dimensions of the digital substructure from the digital denture design to form a digital mating cavity; and
 c) an automated manufacturing system for performing a sequence of manufacturing instructions for producing a denture shape comprising a mating cavity and a substructure from the digital denture design and the digital substructure design.

In a further embodiment, the system further comprises an additive manufacturing system for producing the denture shape, and a subtractive manufacturing process for producing the substructure based on the digital substructure design.

While the present methods have been described with reference to the above-disclosed embodiments, those skilled in the art will recognize that many changes and variations may be made thereto. Each of these embodiments and variations thereof is contemplated as falling within the present disclosure.

We claim:

1. A method of making an implant-supported denture device for a patient, comprising the steps of:
 a) scanning an edentulous jaw of a patient having dental implants to acquire a first image of the edentulous jaw and a provisional denture device that is attached the edentulous jaw, wherein the edentulous jaw is a mandibular arch;
 b) removing the provisional denture device from the jaw and attaching digital impression copings to a plurality of dental implants implanted in the edentulous jaw, and scanning the patient's edentulous jaw to acquire a second image of the edentulous jaw and the digital impression copings;
 c) scanning a jaw opposing the edentulous jaw, wherein the opposing jaw comprises dentition, to acquire a third image of the opposing jaw and dentition;
 d) saving the first, second, and third images into an electronic storage medium;
 e) registering the images using at least one oral landmark selected from a retromolar pad and a mandibular torus common to the first and second image, and creating a digital patient model;
 f) forming i. a digital denture design that comprises digital denture teeth and a gingiva region, and ii. a digital substructure design, based on the digital patient model;
 g) manufacturing a substructure based on the digital substructure design using an automated manufacturing process, and manufacturing a denture shape with a cavity corresponding to the substructure from the digital denture design using an automated manufacturing process;
 h) assembling the denture shape and the substructure to form an assembly; and
 i) fabricating the implant-supported denture device from the assembly.

2. The method of claim 1, additionally comprising making an implant-supported denture device for a maxillary arch of a patient by the method, wherein edentulous jaw is a maxillary arch, and the at least one oral landmark is selected from a maxillary tuberosity, a hamular notch and an incisive papilla.

3. The method of claim 1, wherein the automated manufacturing process for manufacturing the denture shape is 3D printing.

4. The method of claim 1, wherein the automated manufacturing process for manufacturing the substructure is a subtractive process.

5. The method of claim 1, wherein the automated manufacturing process for manufacturing the substructure is a milling process.

6. The method of claim 1, wherein the automated manufacturing process for manufacturing the substructure is an additive manufacturing process.

7. The method of claim 1 wherein the material for affixing the denture teeth to the substructure forms a gingival denture structure.

8. The method of claim 1 wherein the assembly comprises the implant-supported denture device.

9. The method of claim 1, wherein the step of fabricating an implant-supported denture comprises fabricating a final denture device.

10. A method for making a digital denture design for an implant-supported denture device comprising:
 a) acquiring a dataset of a first image of a patient's oral anatomy comprising an edentulous jaw having implants implanted in the jaw, and a plurality of digital impression copings attached to implants that have at least one surface feature indicating the position and orientation of the implants, and at least one oral landmark;

b) acquiring a dataset of a second image comprising the edentulous jaw, a provisional denture device of the patient attached to the edentulous jaw, and at least one oral landmark;

c) acquiring a dataset of a third image of the patient's oral anatomy comprising a jaw opposing the edentulous jaw that comprises dentition;

d) identifying at least one common oral landmark in the datasets of the first and second Images;

e) registering the first image, the second, and the third image to obtain a digital model of the patient's oral anatomy; and f) generating a digital denture design based on the digital model of the patient's oral anatomy; wherein the digital denture design comprises an upper side comprising digital denture teeth and digital gingiva, and a lower side comprising a digital surface corresponding to the edentulous jaw, and g) generating a digital substructure design corresponding to the digital model of the patient's oral anatomy, and designing the digital denture design to comprise a mating cavity on the lower side corresponding to the dimensions of the digital substructure design.

11. The method of claim 10, wherein the step of generating a digital denture design comprises subtracting a digital data set that corresponds to digital substructure from the digital denture design.

12. The method of claim 10 wherein the first image and the second image each comprise a common anterior oral landmark and at least one common posterior oral landmark.

13. The method of claim 10, further comprising acquiring a fourth image of the provisional denture device, and registering the fourth image of the provisional denture device with the first, second and third images.

14. The method of claim 13, wherein the first and second images each comprise at least one oral landmark in common selected from a retromolar pad, a maxillary tuberosity, and an incisive papilla, for use in registering the images.

15. A method of making an implant-supported denture device for a patient, comprising the steps of:
   a) scanning an edentulous jaw of a patient having dental implants to acquire a first image of the edentulous jaw and a provisional denture device that is attached the edentulous jaw, wherein the edentulous jaw is a mandibular arch;
   b) removing the provisional denture device and attaching digital impression copings to a plurality of dental implants implanted in the edentulous jaw, and scanning the patient's jaw to acquire a second image of the edentulous jaw and the digital impression copings;
   c) scanning a jaw opposing the edentulous jaw, wherein the opposing jaw comprises dentition, to acquire a third image of the opposing jaw and dentition;
   d) saving the first, second, and third images into an electronic storage medium;
   e) registering the first and second images using at least one oral landmark selected from a retromolar pad and a mandibular torus common to the first and second image, and creating a digital patient model;
   f) forming a digital denture design from the digital patient model, that comprises digital denture teeth and a gingiva region; and
   g) manufacturing an implant-supported final denture device from the digital denture design using an automated manufacturing process wherein the denture shape comprises a monolithic ceramic portion comprising a monolithic denture teeth region and a denture gingiva region.

16. The method of claim 15 wherein the monolithic ceramic portion comprises zirconia.

17. The method of claim 15, additionally comprising making an implant-supported denture device for a maxillary arch of a patient by the method, wherein the first and second images of a second edentulous jaw that is a maxillary arch comprise at least one common oral landmark selected from a hamular notch, an incisive papilla, and a maxillary tuberosity.

18. A method of making an implant-supported denture device for a patient, comprising the steps of:
   a) scanning an edentulous jaw of a patient having dental implants to acquire a first image of the edentulous jaw and a provisional denture device that is attached the edentulous jaw, wherein the edentulous jaw is a maxillary arch;
   b) removing the provisional denture device and attaching digital impression copings to a plurality of dental implants implanted in the edentulous jaw, and scanning the patient's jaw to acquire a second image of the edentulous jaw and the digital impression copings;
   c) scanning a jaw opposing the edentulous jaw, wherein the opposing jaw comprises dentition, to acquire a third image of the opposing jaw and dentition;
   d) saving the first, second, and third images into an electronic storage medium;
   e) registering the first and second images using at least one oral landmark common to the first and second image, selected from a hamular notch, an incisive papilla, and a maxillary tuberosity, and creating a digital patient model;
   f) forming a digital denture design from the digital patient model, that comprises digital denture teeth and a gingiva region; and
   g) manufacturing an implant-supported final denture device from the digital denture design using an automated manufacturing process wherein the denture shape comprises a monolithic ceramic portion comprising a monolithic denture teeth region and a denture gingiva region.

19. The method of claim 18 wherein the monolithic ceramic portion comprises zirconia.

20. A method of making an implant-supported denture device for a patient, comprising the steps of:
   a) scanning an edentulous jaw of a patient having dental implants to acquire a first image of the edentulous jaw and a provisional denture device that is attached the edentulous jaw, wherein the edentulous jaw is a maxillary arch;
   b) removing the provisional denture device from the jaw and attaching digital impression copings to a plurality of dental implants implanted in the edentulous jaw, and scanning the patient's edentulous jaw to acquire a second image of the edentulous jaw and the digital impression copings;
   c) scanning a jaw opposing the edentulous jaw, wherein the opposing jaw comprises dentition, to acquire a third image of the opposing jaw and dentition;
   d) saving the first, second, and third images into an electronic storage medium;
   e) registering the images using at least one oral landmark selected from a maxillary tuberosity, a hamular notch and an incisive papilla common to the first and second image, and creating a digital patient model;

f) forming i. a digital denture design that comprises digital denture teeth and a gingiva region, and ii. a digital substructure design, based on the digital patient model;
g) manufacturing a substructure based on the digital substructure design using an automated manufacturing process, and manufacturing a denture shape with a cavity corresponding to the substructure from the digital denture design using an automated manufacturing process;
h) assembling the denture shape and the substructure to form an assembly; and
i) fabricating the implant-supported denture device from the assembly.

21. The method of claim 20, wherein the automated manufacturing process for manufacturing the denture shape is 3D printing.

22. The method of claim 20, wherein the automated manufacturing process for manufacturing the substructure is a subtractive process.

* * * * *